US009518896B2

(12) United States Patent
Zeng et al.

(10) Patent No.: US 9,518,896 B2
(45) Date of Patent: Dec. 13, 2016

(54) GRADUALLY-ASCENDING SPIRALED PASSIVE SAMPLER FOR MEASURING SEDIMENT-WATER DIFFUSION FLUX OF ORGANIC POLLUTANTS

(71) Applicant: Guangzhou Institute of Geochemistry, Chinese Academy of Sciences, Guangzhou (CN)

(72) Inventors: Eddy Y. Zeng, Guangzhou (CN); Shiping Xu, Guangzhou (CN); Huihui Liu, Guangzhou (CN)

(73) Assignee: Guangzhou Institute of Geochemistry, Chinese Academy of Sciences, Guangzhou (CN)

( * ) Notice: Subject to any disclaimer, the term of this patent is extended or adjusted under 35 U.S.C. 154(b) by 825 days.

(21) Appl. No.: 13/882,216

(22) PCT Filed: Jan. 9, 2013

(86) PCT No.: PCT/CN2013/070256
§ 371 (c)(1),
(2) Date: Apr. 29, 2013

(87) PCT Pub. No.: WO2014/089921
PCT Pub. Date: Jun. 19, 2014

(65) Prior Publication Data
US 2014/0165712 A1 Jun. 19, 2014

(30) Foreign Application Priority Data
Dec. 14, 2012 (CN) .......................... 2012 1 0545905

(51) Int. Cl.
*G01N 1/10* (2006.01)
*G01N 33/18* (2006.01)

(52) U.S. Cl.
CPC ............. *G01N 1/10* (2013.01); *G01N 33/1826* (2013.01); *G01N 2001/1025* (2013.01); *G01N 2001/1031* (2013.01)

(58) Field of Classification Search
CPC ............... B01D 25/04; C02F 2201/007; G01N 33/1806; G01N 2001/1031; G01N 2001/1025; G01N 2001/4083; G01N 1/20; G01N 1/10
(Continued)

(56) References Cited

U.S. PATENT DOCUMENTS 5,085,085 A * 2/1992 Anderson ................ G01N 1/02
73/863.02
6,295,867 B1 * 10/2001 Mahaffey ................ E21B 17/16
73/152.02
(Continued)

FOREIGN PATENT DOCUMENTS

CN 102183382 * 6/2009 ............... G01N 1/10
CN 101446539 * 9/2011 ............. G01N 13/00
(Continued)

OTHER PUBLICATIONS

English machine translation for CN 1021833822.*
(Continued)

*Primary Examiner* — Peter Macchiarolo
*Assistant Examiner* — Anthony W Megna Fuentes
(74) *Attorney, Agent, or Firm* — Dority & Manning, P.A.

(57) ABSTRACT

The present invention discloses a gradually-ascending spiraled passive sampler for measuring sediment-water diffusion flux of organic polutants, which comprises a sediment pore-water sampler and a water sampler arranged above the sediment pore-water sampler, wherein a plurality of sediment sampling units are vertically arranged in the sediment pore-water sampler, and the water sampler is provided with
(Continued)

a plurality of water sampling units arranged transversely along the vertical direction in sequence.

8 Claims, 5 Drawing Sheets

(58) Field of Classification Search
USPC .................. 73/863.23, 64.56, 863.21, 61.63
See application file for complete search history.

(56) References Cited

U.S. PATENT DOCUMENTS

| | | | |
|---|---|---|---|
| 6,416,674 B1* | 7/2002 | Singleton | E03F 5/105 |
| | | | 210/163 |
| 6,495,375 B2* | 12/2002 | Ledig | G01N 33/0011 |
| | | | 436/174 |
| 6,742,406 B2* | 6/2004 | Dostie | G01N 15/04 |
| | | | 73/864.64 |
| 7,430,929 B1* | 10/2008 | Vroblesky | E02D 1/06 |
| | | | 73/863.23 |

FOREIGN PATENT DOCUMENTS

| | | |
|---|---|---|
| WO | WO 2009111161 A2 | 9/2009 |
| WO | WO 2009111161 A3 | 9/2009 |

OTHER PUBLICATIONS

English machine translation for CN 101446539.*
Abstract of Chinese Patent—CN101446539, Jun. 3, 2009, 1 page.
Abstract of Chinese Patent—CN101608982, Dec. 26, 2009, 1 page.
Abstract of Chinese Patent—CN102183362, Sep. 14. 2011, 1 page.
Abstract of Chinese Patent—CN202281703, Jun. 20, 2012, 1 pages.
International Search Report for PCT/CN2013/070256 dated Sep. 16. 2013, 2 pages.

* cited by examiner

GRADUALLY-ASCENDING SPIRALED PASSIVE SAMPLER FOR MEASURING SEDIMENT-WATER DIFFUSION FLUX OF ORGANIC POLLUTANTS

CROSS REFERENCE TO RELATED APPLICATION

This application is the national stage entry of International Patent Application No. PCT/CN2013/070256 having a filing date of Jan. 9, 2013, which claims priority to and the benefit of Chinese Patent Application No. 201210545905.8 filed in the Chinese Intellectual Property Office on Dec. 14, 2012, the entire contents of which are Incorporated herein by reference.

FIELD OF TECHNOLOGY

The present invention relates to the technical field of water sampling, especially to a gradually-ascending spiraled passive sampler for measuring sediment-water diffusion flux of organic pollutants.

BACKGROUND OF THE INVENTION

Persistent organic pollutant refers to hydrophobic organic substance of high toxicity which remains, migrates in the environment for a long time, and accumulates in organism, the persistent organic pollutant is mainly remained in organic phase of sediment in natural environment, so that, the pollutant concentration in sediment pore water is higher than that in the water, Meanwhile, the persistent organic pollutant constantly diffuses to overlaying water and cycles in the ecological system through evaporation, dissolution, adsorption and organism absorption etc. A correct assessment of the exchange flux of the hydrophobic pollutant between the sediment pore water and the overlaying water is highly necessary since the hydrophobic organic substance is potentially harmful to the organism.

In the prior art, the traditional method is to measure the concentration of the organic substance in the sediment and water respectively, and then make a comparison and estimates the diffusion direction and flux of the organic pollutant.

Alternatively, a method for measuring flux in situ is adopted, in which, a flux test box is arranged in situ and the content of the target substance in the adsorbent within the test box is measured after a period of time according to the passive diffusion principle, and then the diffusion flux is estimated according to an balanced partition coefficient.

In the prior art, though the traditional method is simple, convenient and direct, it has the following disadvantages: first, it can only determine data of single point of pore water and overlaying water and is hard to exactly reflect the characteristics of the concentration change; second, the estimation of the interface flux is based on the hypothesis that the concentration gradient is linear, which does not accord with the theoretical calculation and the actual situation; third, the measurement of the concentration of the organic substance in the sediment pore water and the overlaying water needs a lot of solvate, the recycle rate is low, and the analysis cost is too high.

The method for measuring flux in situ has the advantages of direct diffusion flux measurement and little interference from the environment. However, it also has the following disadvantages: first, the method is to measure a static unidirectional diffusion flux, namely, under the drive of the adsorption of adsorbent, the escaped flux of migration of part of target substance from the sediment or the overlaying water excludes the flux that target substance deposited downward in water, and therefore the outcome is not the balanced flux; second, the flux measured is that in position of the adsorbent other than the complete diffusion flux from the sediment to the water; third, only a single data of at certain depth of the water can be measured.

SUMMARY

The technical problem to be solved by the present invention is to provide a gradually-ascending spiraled passive sampler for measuring sediment-water diffusion flux of organic polutants, which features convenient operation as well as direct, simultaneous and multi-point sampling of organic pollutant in the sediment pore water and the water.

The technical scheme of the present invention to solve the above-mentioned technical problem is: a gradually-ascending spiraled passive sampler for measuring sediment-water diffusion flux of organic polutants, which comprises a sediment pore-water sampler and a water sampler arranged above the sediment pore-water sampler, wherein, a plurality of sediment sampling units are vertically arranged in the sediment pore-water sampler, and the water sampler is provided with a plurality of water sampling units arranged transversely along the vertical direction in sequence.

As a further improvement of the present invention, the sediment sampling unit is a grid-shaped sediment sampling plate, which comprises a partition board, filter membranes arranged at two sides of the partition board respectively, and first porous clamping plates arranged outside the filter membrane respectively, wherein a plurality of long-striped openings are transversely formed in the partition board in a separated and parallel manner, and adsorption films are arranged in the openings.

As a further improvement of the present invention, the sediment pore-water sampler comprises a plurality of grid-shaped sediment sampling plates which are spliced together and adjacent to each other.

As a further improvement of the present invention, the water sampling unit comprises an adsorption film, filter membrane arranged at two sides of the adsorption film respectively, and second porous clamping plates arranged outside the filter membrane respectively.

As a further improvement of the present invention, the water sampling units are spirally arranged within the water sampler upwardly in sequence, around the center of the water sampler.

As a further improvement of the present invention, the pitches between the water sampling units arranged upwardly in sequence increase gradually.

As a further improvement of the present invention, the water sampler comprises a support member arranged at the upper end of the sediment pore-water sampler, a central support pillar arranged in the center and side support pillars arranged at the end of the support separately, and a fixing member arranged at the upper end of the central support pillar and the side support pillar, and the water sampling unit is arranged between the central support pillar and the side support pillar.

As a further improvement of the present invention, round holes are formed at the two ends of a diagonal line of the second porous clamping plate and are fitted with the central support pillar and the side support pillar, spacer rings of different heights for supporting the second porous clamping plate are mounted on the central support pillar and the side support pillar, and the second porous clamping plate is clamped between adjacent spacer rings on the central support pillar and those on the side support pillar by means of the round hole.

As a further improvement of the present invention, the adsorption film is a polyethylene adsorption film, and the filter membrane is a fiberglass filter membrane.

The beneficial effects are: by combining the sediment pore-water sampler and the water sampler together judiciously, arranging the sediment sampling units vertically in the sampler for the sediment pore water, and arranging the plurality of water sampling units transversely in the water sampler along the vertical direction in sequence, the gradually-ascending spiraled passive sampler for measuring sediment-water diffusion flux of organic polutants can simultaneously acquire the exact concentration of the organic pollutant in the sediment pore water in the same position but at different depths those in the overlaying water at different heights, namely, a multi-point measurement of the concentration of the sediment pore water and the overlaying water in different positions can be performed at the same time, thus the real gradient change of the concentration in different phases of the interface of sediment and water can be acquired, and then the real diffusion flux between the sediment pore water and the overlaying water can be acquired through mathematical calculation and processing.

BRIEF DESCRIPTION OF DRAWINGS

A further description will be made to the present invention with reference to the drawings and embodiments.

DETAILED DESCRIPTION OF THE EMBODIMENTS

Referring to FIGS. 1 to 5, the present invention is a gradually-ascending spiraled passive sampler for measuring sediment-water diffusion flux of organic polutants, comprising a sediment pore-water sampler 2 and a water sampler 1 arranged above the sediment pore-water sampler 2, wherein a plurality of sediment sampling units 4 are vertically arranged in the sediment pore-water sampler 2, and the water sampler 1 is provided with a plurality of water sampling units arranged transversely along the vertical direction in sequence.

Figure 1:
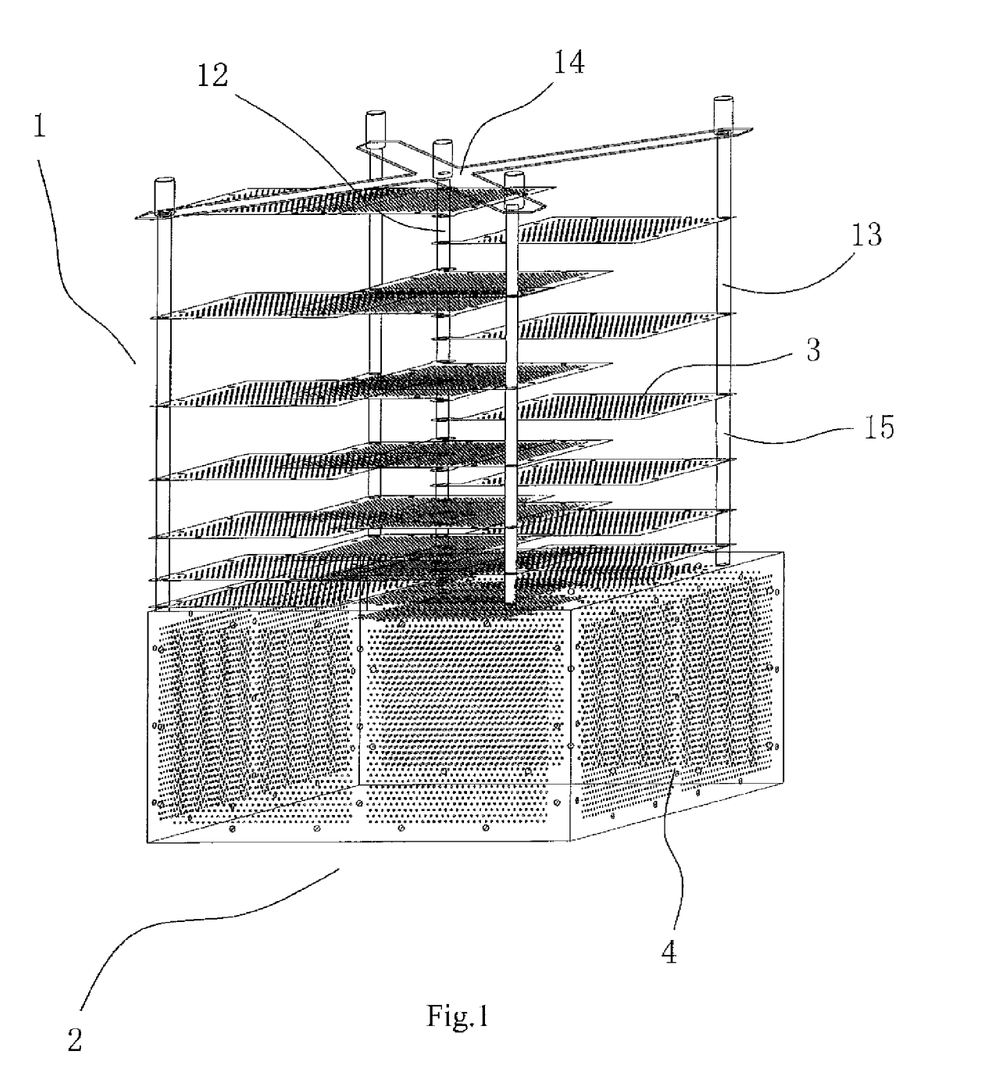
FIG. 1 is a structural view of the present invention.

By combining the sediment pore-water sampler 2 and the water sampler 1 together judiciously, arranging the sediment sampling units 4 vertically in the sampler for the sediment pore water 2, and arranging the plurality of water sampling units 3 transversely in the water sampler 1 along the vertical direction in sequence, the gradually-ascending spiraled passive sampler for measuring sediment-water diffusion flux of organic polutants can simultaneously acquire the exact concentration of the organic pollutant in the sediment pore water in the same position but at different depths those in the overlaying water at different heights. Namely, a multi-point measurement of the concentration of sediment pore water and overlaying water in different positions can be performed at the same time, thus the real gradient change of concentration in different phases of sediment-water interface can be acquired, and then, the real diffusion flux between the sediment pore water and the overlaying water can be acquired through mathematical calculation and processing.

The method for measuring flux in situ in the prior art can only measure the unidirectional diffusion flux from the sediment pore water to the overlaying water at a certain water depth, but cannot measure the balanced diffusion flux and also cannot acquire the data of concentration of the organic pollutant in sediment pore water at the measuring-site.

With regard to sampling and extracting of the organic pollutant at the sediment pore water and the overlaying water, passive adsorption of organic pollutant can be realized by means of the sediment sampling unit 4 and the water sampling unit 3, so that the complicated and time-consuming operations, such as the collection of a great number of samples, centrifugal separation, solvent extraction, ultrasonic extraction and the like can be eliminated, the cost of sample collection and pre-processing is greatly reduced, and the data analysis efficiency and data accuracy are greatly improved.

Figure 4:
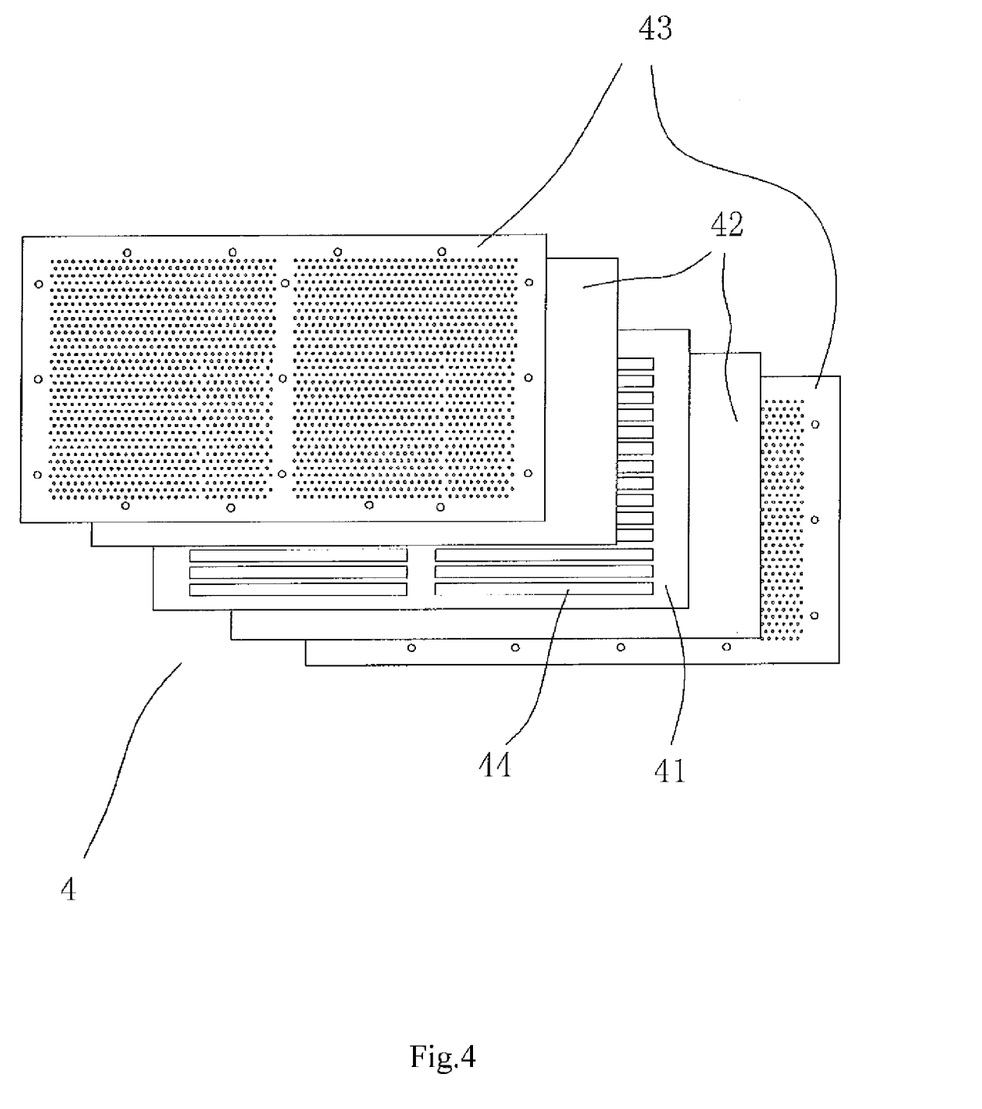
FIG. 4 is a structural view of the sediment sampling unit of the present invention.

As a preferred embodiment of the present invention, the sediment sampling unit 4 is a grid-shaped sediment sampling plate, which comprises a partition board 41, filter membranes 42 arranged at two sides of the partition board 41 respectively, and first porous clamping plates 43 arranged outside the filter membranes 42 respectively. A plurality of long-striped openings are transversely formed in the partition board 41 in a separated and parallel manner, and adsorption films 44 are arranged in the openings.

The partition board 41 and the first porous clamping plate 43 are made of stainless steel plate, and the plurality of long strip-shaped openings transversely formed in the partition board 41 in a separated and parallel manner forms a plurality of hollow frames in the partition board 41. The hollow frames are provided with the adsorption films 44 whose number and size are matched with that of the hollow frames in the partition board 41. The filter membrane 42 is pasted to the two sides of the partition board 41 which is provided with the adsorption film 44, and the first porous clamping plates 43 are further arranged outside of the filter membrane 42. The partition board 41, the filter membrane 42 and the first porous clamping plate 43 are fastened in sequence through a stainless steel screw component and assembled to a grid-shaped sediment sampling plate in the form of a single-sheet. The first porous clamping plates 43 give support and protection to the adsorption film 44 and the filter membrane 42 to keep them vertical, so that the accuracy of data is improved. The filter membrane 42 is used to filter particles and form a certain water-bearing space between the adsorption film 44 and the first porous clamping plate 43, so as to facilitate the diffusion and exchange of organic pollutant in the adsorption film 44 and the water.

Figure 5:
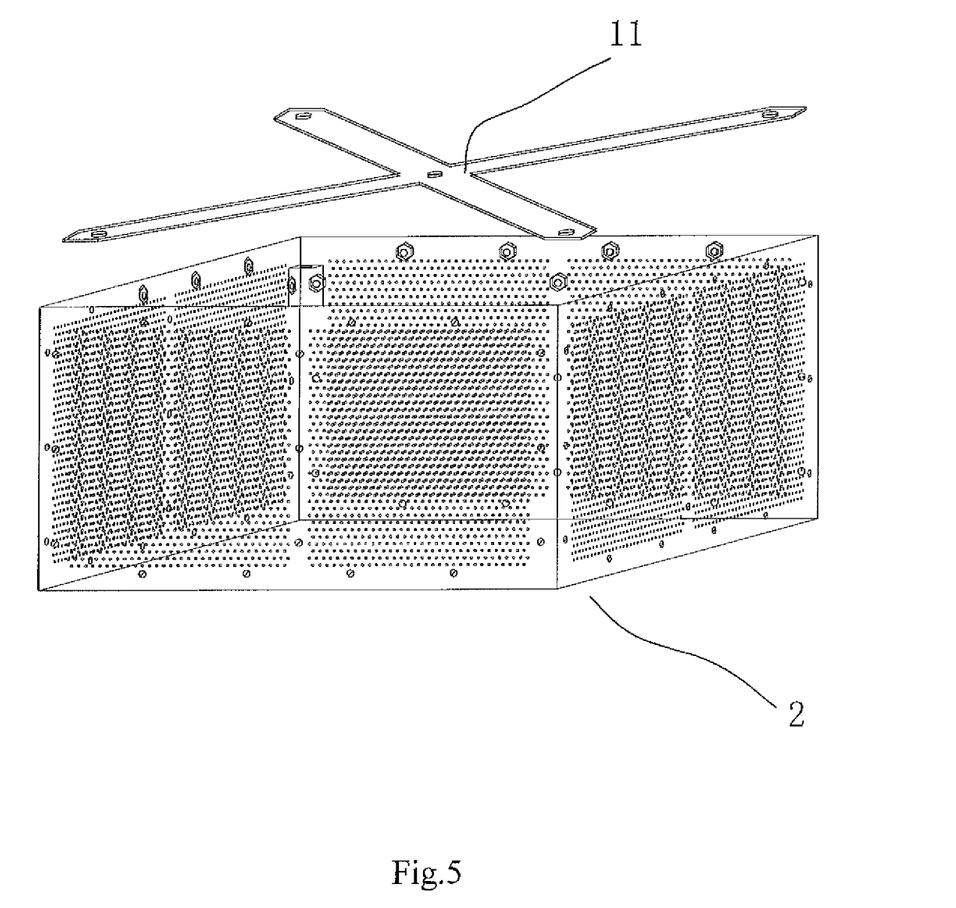
FIG. 5 is a structural view of the sediment pore-water sampler of the present invention.

As a preferred embodiment of the present invention, the sediment pore-water sampler 2 comprises a plurality of grid-shaped sediment sampling plates which are spliced together and adjacent to each other.

The sediment pore-water sampler 2 is formed by splicing four pieces of grid-shaped sediment sampling plate, stainless angle steel is adopted to connect and fix the splicing place of the grid-shaped sediment sampling plate.

Figure 2:
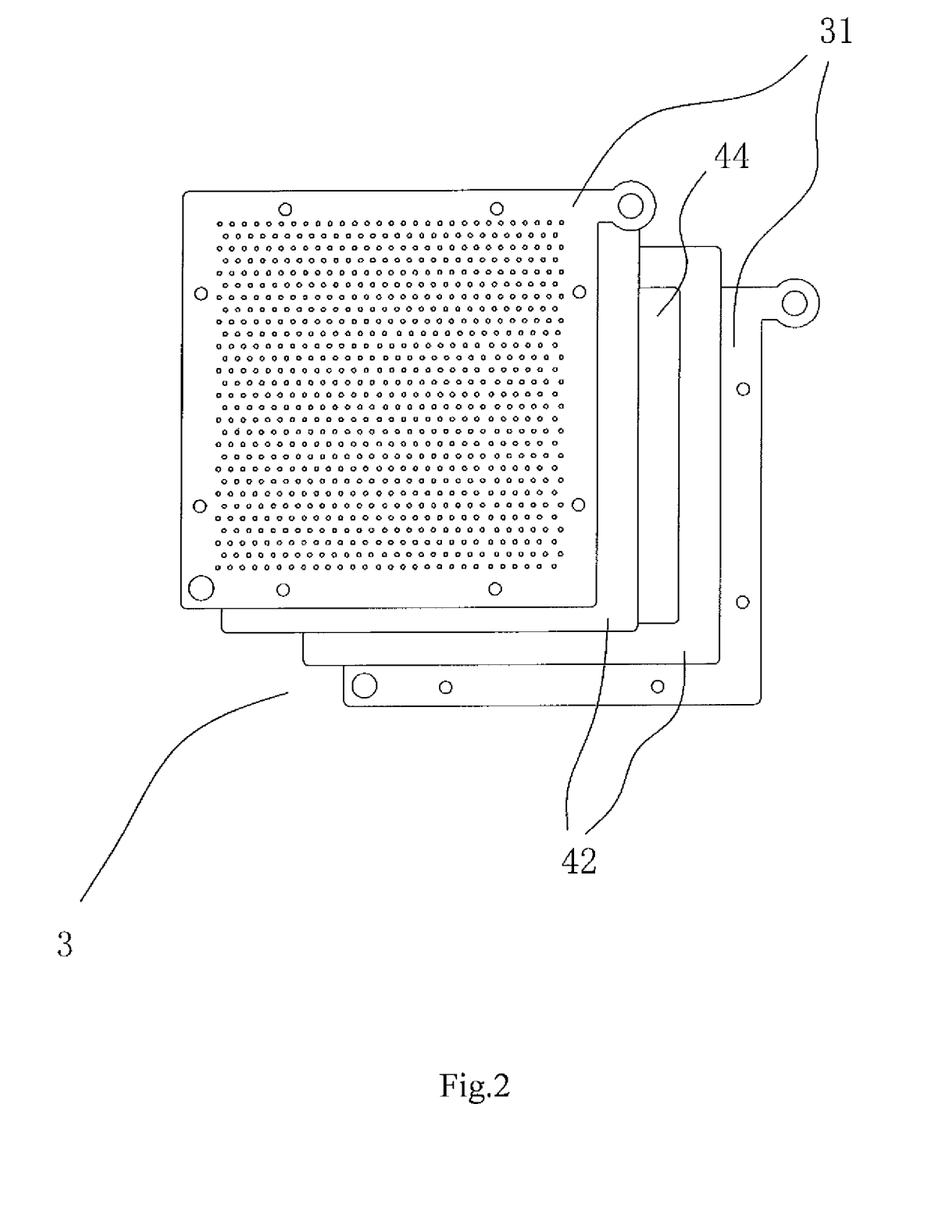
FIG. 2 is a structural view of the water sampling unit of the present invention.

As a preferred embodiment of the present invention, the water sampling unit 3 comprises an adsorption film 44, filter membranes 42 arranged at two sides of adsorption film 44 respectively, and second porous clamping plates 31 arranged outside the filter membrane 42.

The adsorption film 44, the filter membranes 42 and the second porous clamping plates 31 are fastened through a stainless steel screw component and assembled to form the water sampling unit 3 of a single-sheet shape. The second porous clamping plates 31 give support and protection to the adsorption film 44 and the filter membrane 42 to keep them vertical, so that the accuracy of data is improved. The filter membranes 42 is used to filter particles and form a certain water-bearing space between the adsorption film 44 and the second porous clamping plate 31, so as to facilitate the diffusion and exchange of organic pollutant in the adsorption film 44 and the water.

Figure 3:
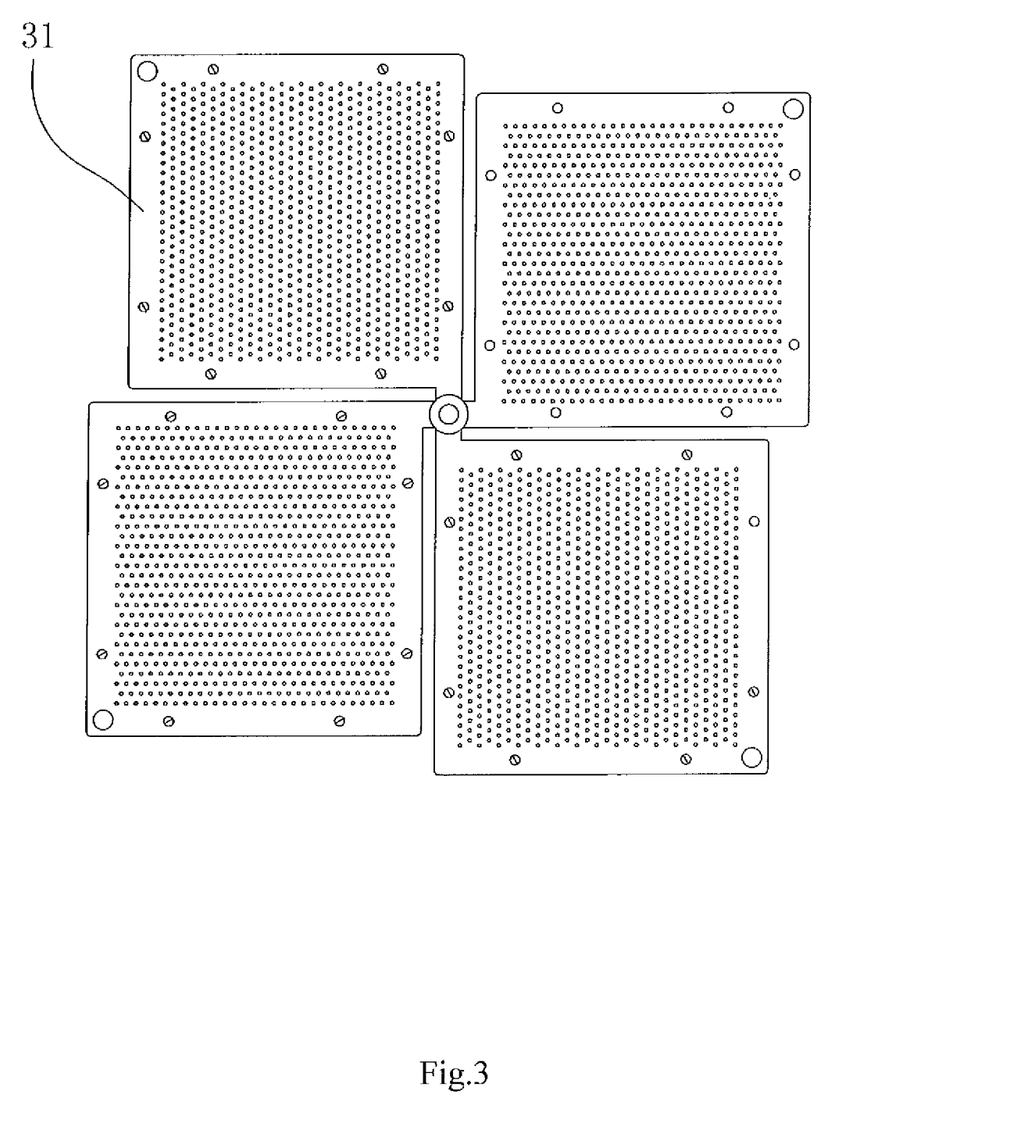
FIG. 3 is a structural view of a combination of water sampling units of the present invention.

As a preferred embodiment of the present invention, the water sampling units 3 are spirally arranged within the water sampler 1 in sequence upwardly, around the center of the water sampler 1. As a preferred embodiment of the present invention, the pitches between the water sampling units 3 arranged upwardly in sequence increase gradually.

The concentration change of the organic pollutant in the vertical direction is non-linear in overlaying water, and therefore, adjacent water sampling units 3 are spaced and arranged according to an arithmetic progression along the vertical direction. The water sampling unit 3 is arranged spirally in sequence around the central axis of the water sampler 1, and the pitch between the water sampling units 3 arranged in sequence increases gradually according to an arithmetic progression. The water sampling unit 3 adopts this gradually-ascending spiral arrangement, so that the pitch between the spaced water sampling units 3 in the same vertical direction can be increased more than three times, and the negative error caused by the depletable interference between two spaced water sampling units 3 in the height direction can be reduced and eliminated.

As a preferred embodiment of the present invention, the water sampler 1 comprises a support member 11 arranged at the upper end of the sediment pore-water sampler 2, a central support pillar 12 arranged in the center and side support pillars 13 arranged separately at the ends of the support member 11, and a fixing member 14 arranged at the upper end of the central support pillar 12 and the side support pillar 13. The water sampling unit 3 is arranged between the central support pillar 12 and the side support pillar 13.

The support member 11 is a cross-shaped support made of stainless steel and mounted at the upper end of the sediment pore-water sampler 2 to support the water sampling unit 3, the central support pillar 12 is mounted in the center of the cross-shaped support, four side support pillars 13 are mounted at the four ends of the cross-shaped support, and the central support pillar 12 and the side support pillar 13 are used to support the water sampling unit 3 which is arranged in the form of a gradually-ascending spiral. The fixing member 14 is also a cross-shaped support made of stainless steel and corresponding to the support member 11. The fixing member 14 is used to fix the central support pillar 12 and the side support pillar 13 with a screw cap.

As a preferred embodiment of the present invention, round holes are formed at the two ends of a diagonal line of the second porous clamping plate 31 and fitted with the central support pillar 12 and the side support pillar 13, spacer rings 15 of different heights for supporting the second porous clamping plate 31 are mounted on the central support pillar 12 and the side support pillar 13, and the second porous clamping plate 31 is clamped between adjacent spacer rings 15 on the central support pillar 12 and those on the side support pillar 13 by means of the round hole.

Spacer rings 15 of different heights are mounted on the central support pillar 12 and the side support pillar 13. Round holes corresponding to the central support pillar 12 and the side support pillar 13 in size are formed at the two ends of a diagonal line of the second porous clamping plate 31. The second porous clamping plate 31 is fitted onto the central support pillar 12 and the side support pillar 13 through the round holes 31, so as to be clamped between adjacent spacer rings 15, and mounted between the central support pillar 12 and the side support pillar 13. By combining and arranging the spacer rings 15 of different heights, water sampling units 3 is fixed at predetermined heights within the water sampler 1 with a gradually-ascending spiraled arrangement between the central support pillar 12 and the side support pillar 13.

As a preferred embodiment of the present invention, the adsorption film 44 is a polyethylene adsorption film, and the filter membrane 42 is a fiberglass filter membrane.

In the passive water sampler of the present invention, the polyethylene adsorption film arranged in the sediment sampling unit 4 and the water sampling unit 3 is used as an adsorbent to carry out the in situ adsorption of the persistent organic pollutant. After the sample adsorbed and sampled is eluted quantitatively from the polyethylene adsorption film with organic solvent, qualitative and quantitative analysis is performed with the chromatography-mass spectrometry, and then the real diffusion flux between the sediment pore water and the overlaying water is calculated by mathematics processing based on the analysis data.

While detailed explanation is made to the embodiments of the present invention with reference to accompanying drawings, the present invention is not limited to the above-mentioned embodiments, and various modifications can be made within the knowledge of the ordinary skilled in the art and without departing from the purpose of the present invention.

The invention claimed is:

1. A gradually-ascending spiraled passive sampler for measuring sediment-water diffusion flux of organic pollutants, characterized in that: it comprises a sediment pore-water sampler and a water sampler arranged above the sediment pore-water sampler, wherein a plurality of sediment sampling units are vertically arranged in the sediment pore-water sampler, and the water sampler is provided with a plurality of water sampling units arranged transversely along the vertical direction in sequence, wherein each of the plurality of sediment sampling units is a grid-shaped sediment sampling plate, wherein the sampling plate comprises a partition board, filter membranes arranged at two sides of the partition board respectively, and first porous clamping plates arranged outside the filter membrane, further wherein a plurality of long-striped openings are transversely formed in the partition board in a separated and parallel manner and adsorption films are arranged in the long-striped openings.

2. The gradually-ascending spiraled passive sampler for measuring sediment-water diffusion flux of organic pollutants according to claim 1, characterized in that: the sediment pore-water sampler comprises a plurality of sediment grid-shaped sampling plates which are spliced together and adjacent to each other.

3. The gradually-ascending spiraled passive sampler for measuring sediment-water diffusion flux of organic pollutants according to claim 1, characterized in that: each of the plurality of water sampling units comprises an adsorption film, filter membranes arranged at two sides of adsorption film respectively, and second porous clamping plates arranged outside the filter membrane respectively.

4. The gradually-ascending spiraled passive sampler for measuring sediment-water diffusion flux of organic pollutants according to claim 3, characterized in that: the water sampling units are spirally arranged within the water sampler in sequence upwardly, around a center of the water sampler.

5. The gradually-ascending spiraled passive sampler for measuring sediment-water diffusion flux of organic pollutants according to claim 4, characterized in that: pitches between the water sampling units are arranged upwardly in sequence and increase gradually.

6. The gradually-ascending spiraled passive sampler for measuring sediment-water diffusion flux of organic pollutants according to claim 4, characterized in that: the water sampler comprises a support member arranged at an upper end of the sediment pore-water sampler, a central support pillar arranged in a center of the support member and a side support pillar arranged at an end of the support member separately, and a fixing member arranged at an upper end of the central support pillar and the side support pillar; wherein the plurality of water sampling units are arranged between the central support pillar and side support pillar.

7. The gradually-ascending spiraled passive sampler for measuring sediment-water diffusion flux of organic pollutants according to claim 6, characterized in that: round holes are formed at two ends of a diagonal line of the second porous clamping plate and are fitted with the central support pillar and the side support pillar; spacer rings of different heights for supporting the second porous clamping plate are mounted on the central support pillar and the side support pillar; and the second porous clamping plates are clamped between adjacent spacer rings on the central support pillar and those on the side support pillar by means of the round hole.

8. The gradually-ascending spiraled passive sampler for measuring sediment-water diffusion flux of organic pollutants according to claim 3, characterized in that: the adsorption film is a polyethylene adsorption film, and the filter membrane is a fiberglass filter membrane.

\* \* \* \* \*